(12) United States Patent
Saha

(10) Patent No.: US 9,498,174 B2
(45) Date of Patent: Nov. 22, 2016

(54) WHOLE BODY RF COIL FOR PET-MR SYSTEM

(71) Applicant: General Electric Company, Schenectady, NY (US)

(72) Inventor: Saikat Saha, Waukesha, WI (US)

(73) Assignee: General Electric Company, Schenectady, NY (US)

(*) Notice: Subject to any disclaimer, the term of this patent is extended or adjusted under 35 U.S.C. 154(b) by 409 days.

(21) Appl. No.: 13/727,743

(22) Filed: Dec. 27, 2012

(65) Prior Publication Data

US 2014/0187909 A1 Jul. 3, 2014

(51) Int. Cl.
*A61B 6/00* (2006.01)
*A61B 5/00* (2006.01)
*A61B 6/03* (2006.01)
*A61B 5/055* (2006.01)

(52) U.S. Cl.
CPC ............ *A61B 6/4417* (2013.01); *A61B 5/0035* (2013.01); *A61B 6/037* (2013.01); *A61B 5/055* (2013.01)

(58) Field of Classification Search
CPC ... A61B 6/4417; A61B 5/0035; A61B 5/055
See application file for complete search history.

(56) References Cited

U.S. PATENT DOCUMENTS

| 4,763,076 A * | 8/1988 | Arakawa et al. ............. 324/322 |
| 6,522,144 B2 | 2/2003 | Boskamp |
| 6,885,194 B2 | 4/2005 | Boskamp |
| 7,109,712 B2 | 9/2006 | Boskamp |
| 2006/0238198 A1 * | 10/2006 | Nabetani ....................... 324/318 |
| 2008/0129298 A1 * | 6/2008 | Vaughan et al. .............. 324/322 |
| 2013/0293232 A1 * | 11/2013 | Boskamp et al. ............ 324/318 |

OTHER PUBLICATIONS

Nathan Blow (Functional Neuroscience: How to get ahead in imaging, Nature 458, 925-928, Apr. 16, 2009; Published online Apr. 15, 2009.*
Wiggins et al. (A 7 Tesla Gradient Mode Birdcage Coil for Improved Temporal and Occipital Lobe SNR, Proc. Intl. Soc. Mag. Reson. Med. 14, 2006.*

* cited by examiner

*Primary Examiner* — Bo J Peng

(57) ABSTRACT

A PET-MR apparatus includes an MR imaging system having an RF coil former having inner and outer surfaces, an RF shield formed about the outer surface of the RF coil former, and an RF coil positioned on the inner surface of the RF coil former. The PET-MR apparatus also includes a PET system having a detector array positioned to encircle the bore to acquire PET emissions of the subject of interest and a plurality of RF power cables to provide power to the RF coil. The RF coil of the PET-MR apparatus comprises an RF body coil including a pair of end rings and a plurality of rungs extending between the end rings, wherein the plurality of RF power cables are coupled to one of the pair of end rings, along an outer edge of the one end ring distal from the plurality of rungs.

18 Claims, 3 Drawing Sheets

WHOLE BODY RF COIL FOR PET-MR SYSTEM

BACKGROUND OF THE INVENTION

Embodiments of the invention relate generally to positron emission tomography (PET) and magnetic resonance (MR) imaging, and more specifically, to a hybrid PET-MR system having an RF coil assembly and power coil arrangement for providing power to the RF coil that minimizes loss and attenuation of PET signals.

PET imaging involves the creation of tomographic images of positron emitting radionuclides in a subject of interest. A radionuclide-labeled agent is administered to a subject positioned within a detector ring. As the radionuclides decay, positively charged particles known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV.

It is these gamma rays that are detected by the scintillators of the detector ring. When struck by a gamma ray, each scintillator illuminates, activating a photovoltaic component, such as a photodiode. The signals from the photovoltaics are processed as incidences of gamma rays. When two gamma rays strike oppositely positioned scintillators at approximately the same time, a coincidence is registered. Data sorting units process the coincidences to determine which are true coincidence events and sort out data representing deadtimes and single gamma ray detections. The coincidence events are binned and integrated to form frames of PET data which may be reconstructed into images depicting the distribution of the radionuclide-labeled agent and/or metabolites thereof in the subject.

MR imaging involves the use of magnetic fields and excitation pulses to detect the free induction decay of nuclei having net spins. When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a RF magnetic field (excitation field $B_1$) which is in the x-y plane, i.e. perpendicular to the DC magnetic field (B0) direction, and which is near the Larmor frequency, the net aligned moment, or "longitudinal magnetization", $M_Z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

In combination PET-MR systems, the RF coil (i.e., whole body RF coil) that generates the RF magnetic field is typically driven by power cables, also referred to as drive cables. These RF power cables may be as thick as 8 mm in diameter or greater and carry ~30-35 kW of RF power. The RF power cables are typically mounted at the central section of the RF body coil, which is the virtual ground of the RF coil, in order to minimize the shield currents present on the RF power cables. However, mounting the RF power cables at the central section of the RF body coil leads to significant loss/attenuation of PET signals (measured at ~15%), which in turn affects PET image quality.

Other techniques to minimize the shield currents on the cables, such as implementing a quarter wave sleeve and/or employing stub baluns, may be used. However, such workarounds to the issue of shield currents on the RF power cables detrimentally requires much wider bore space, which can pose other significant challenges such as the redesign of the magnet/gradient coil.

It would therefore be desirable to design an RF power cable arrangement that provides power to the RF coil but that minimizes the loss/attenuation of PET singles in the PET-MR system. It would also be desirable to minimize the shield currents present on the RF power cable without the need for additional shielding and/or redesign of the magnet/gradient coil.

BRIEF DESCRIPTION OF THE INVENTION

Embodiments of the invention provide an RF coil assembly and RF power cable arrangement for use in a hybrid PET-MR system.

In accordance with one aspect of the invention, a PET-MR apparatus includes an MR imaging system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest. The PET-MR apparatus also includes a PET system having a detector array positioned to encircle the bore to acquire PET emissions of the subject of interest and a plurality of RF power cables to provide power to the RF coil. The RF coil of the PET-MR apparatus comprises an RF body coil including a pair of end rings and a plurality of rungs extending between the end rings, wherein the plurality of RF power cables are coupled to one of the pair of end rings, along an outer edge of the one end ring distal from the plurality of rungs.

In accordance with another aspect of the invention, a PET-MR apparatus includes an MR imaging system having a plurality of gradient coils positioned about a patient bore, an RF coil former having inner and outer surfaces, an RF shield formed about the outer surface of the RF coil former, and an RF coil configured to emit an RF pulse sequence and receive resulting MR signals from a subject of interest, the RF coil comprising a bird-cage coil positioned on the inner surface of the RF coil former and including a pair of end rings and a plurality of rungs extending between the end rings. The PET-MR apparatus also includes a PET system having a detector array positioned to encircle the bore, with the detector array being controlled to acquire PET emissions of the subject of interest. The PET-MR apparatus further includes an RF power cable arrangement connected to one of the pair of end rings at a plurality of drive points located along an outer edge of the one end ring.

In accordance with yet another aspect of the invention, an RF coil assembly for use in a PET-MR imaging system includes a generally cylindrical RF coil former having an inner surface and an outer surface, an RF shield affixed to the outer surface of the RF coil former, and an RF body coil affixed to an inward facing surface of the RF coil former, with the RF body coil further including a pair of end rings and a plurality of rungs extending between the end rings.

The RF coil assembly also includes a plurality of RF power cables to provide power to the RF body coil, with the plurality of RF power cables being coupled to one of the pair of end rings, along an outer edge of the one end ring distal from the plurality of rungs.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

An RF coil assembly is provided that includes an RF shield and an RF body coil. RF power cables are routed along an outer surface of the RF shield and are connected to an outer edge of an end ring of the RF body coil.

According to embodiments of the invention, the RF coil assembly can be implemented in a variety of imaging systems or apparatuses. For example, the RF coil assembly can be incorporated into a stand-alone MR imaging system or can be incorporated into a hybrid MR imaging system, such as a hybrid PET-MR imaging system, for example. Thus, while embodiments of the invention are set forth here below with respect to a hybrid PET-MR imaging system, it is recognized that other stand-alone and hybrid MR imaging systems are considered to be within the scope of the invention.

Figure 1:
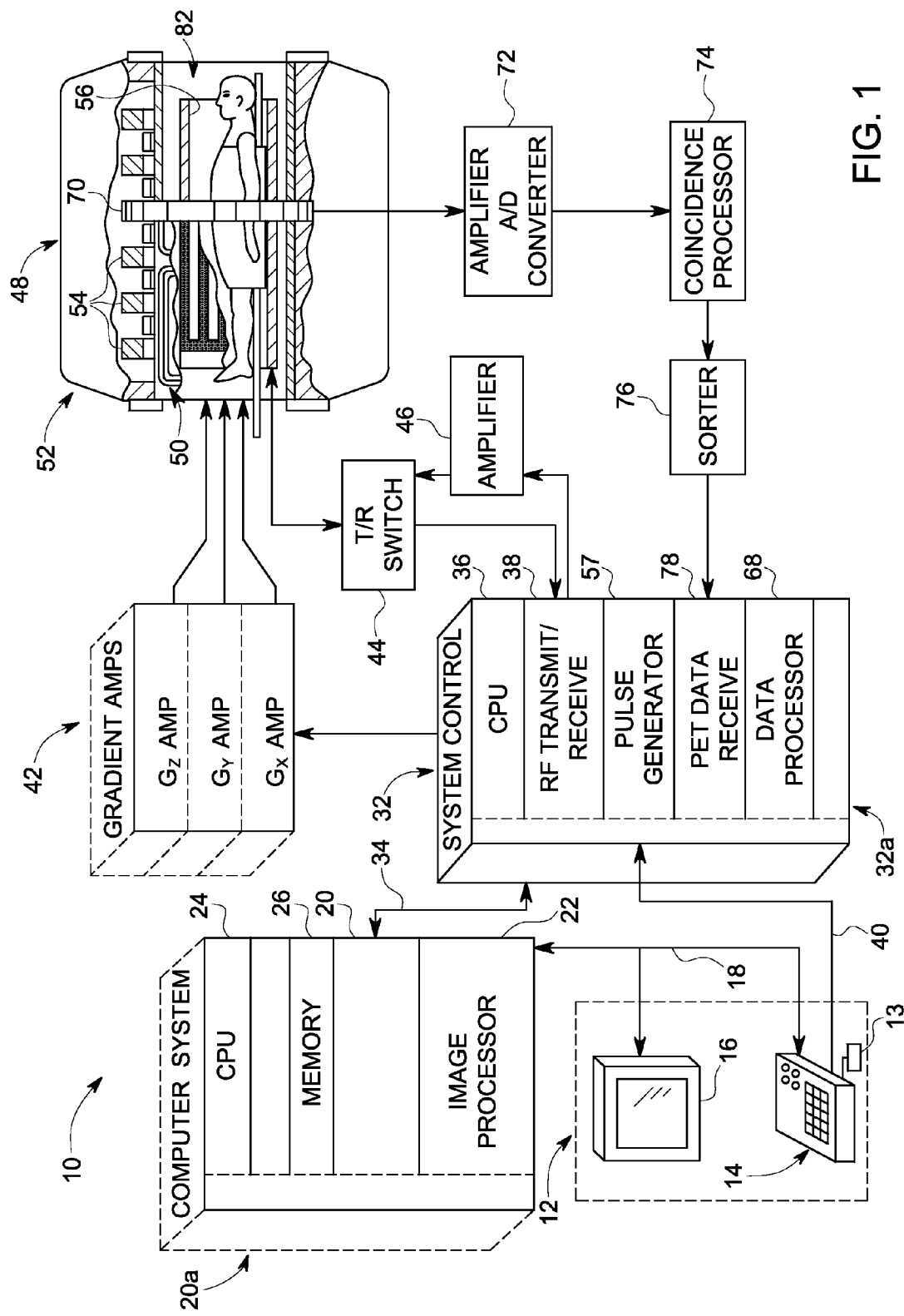
FIG. 1 is a schematic block diagram of an exemplary PET-MR imaging system for use with an embodiment of the invention.

Referring to FIG. 1, the major components of an exemplary hybrid PET-MR imaging system 10 that may incorporate embodiments of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules, such as an image processor module 22, a CPU module 24 and a memory module 26. The computer system 20 may also be connected to permanent or back-up memory storage, a network, or may communicate with a separate system control 32 through link 34. The input device 13 can include a mouse, keyboard, track ball, touch activated screen, light wand, or any similar or equivalent input device, and may be used for interactive geometry prescription.

The system control 32 includes a set of modules in communication with one another and connected to the operator console 12 through link 40. It is through link 34 that the system control 32 receives commands to indicate the scan sequence or sequences that are to be performed. For MR data acquisition, an RF transmit/receive module 38 commands the scanner 48 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 44 and amplifier 46 control the flow of data to scanner 48 from RF transmit module 38 and from scanner 48 to RF receive module 38. The system control 32 also connects to a set of gradient amplifiers 42, to indicate the timing and shape of the gradient pulses that are produced during the scan.

The gradient waveform instructions produced by system control 32 are sent to the gradient amplifier system 42 having Gx, Gy, and Gz amplifiers. Amplifiers 42 may be external of scanner 48 or system control 32, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil 56 (i.e., whole-body RF coil). Alternatively, the gradient coils of gradient coil assembly 50 may be independent of the magnet assembly 52. The coils 56 of the RF coil may be configured for both transmitting and receiving, or for transmit-only or receive-only. A pulse generator 57 may be integrated into system control 32 as shown, or may be integrated into scanner equipment 48, to produce pulse sequences or pulse sequence signals for the gradient amplifiers 42 and/or the RF coil 56. In addition, pulse generator 57 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 56 or by separate receive coils and are then transmitted to the RF transmit/receive module 38 via T/R switch 44. The MR signals are demodulated, filtered, and digitized in the data processing section 68 of the system control 32.

An MR scan is complete when one or more sets of raw k-space data has been acquired in the data processor 68. This raw k-space data is reconstructed in data processor 68 which operates to transform the data (through Fourier or other techniques) into image data. This image data is conveyed through link 34 to the computer system 20 where it is stored in memory 26. Alternatively, in some systems computer system 20 may assume the image data reconstruction and other functions of data processor 68. In response to commands received from the operator console 12, the image data stored in memory 26 may be archived in long term storage or may be further processed by the image processor 22 or CPU 24 and conveyed to the operator console 12 and presented on the display 16.

In combined PET-MR scanning systems, PET data may be acquired simultaneously with the MR data acquisition described above. Thus, scanner 48 also contains a positron emission detector array or ring 70, configured to detect gamma rays from positron annihilation radiations emitted from a subject. Detector array 70 preferably includes a plurality of scintillators and photovoltaics arranged about a gantry. Detector array 70 may, however, be of any suitable construction for acquiring PET data. In addition, the scintillator packs, photovoltaics, and other electronics of the detector array 70 are shielded from the magnetic fields and/or RF fields applied by the MR components 54, 56 by way of an RF shield (not shown), as will be explained in detail below.

Gamma ray incidences detected by detector array 70 are transformed, by the photovoltaics of the detector array 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 26 for subsequent processing 68. PET images may then be reconstructed by image processor 22 and may be combined with MR images to produce hybrid structural and metabolic or functional images. Conditioning circuits 72, coincidence processor 74 and sorter 76 may each be external of scanner 48 or system control 32, or may be integrated therein.

Figure 2:
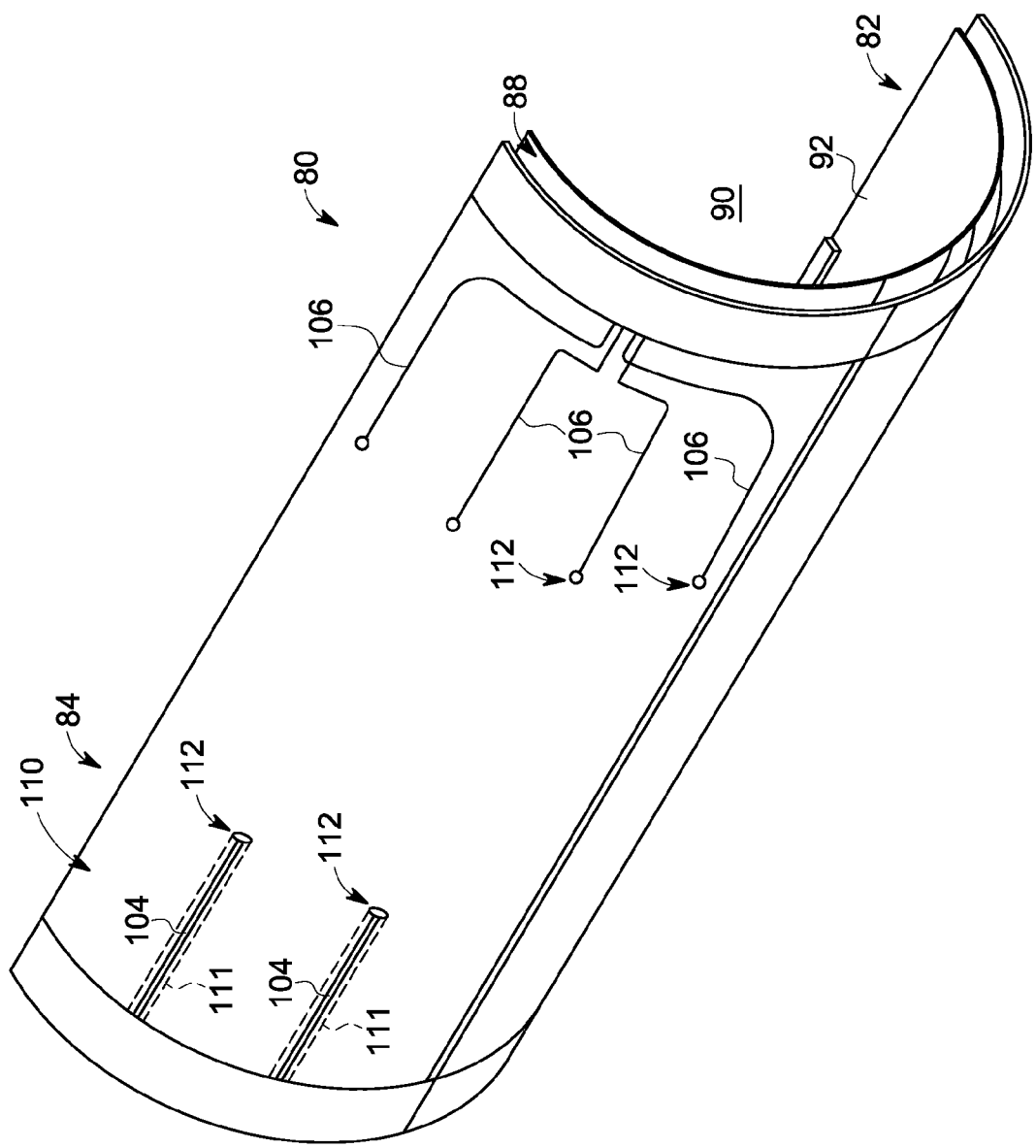
FIGS. 2 and 3 are perspective views of an RF coil assembly for use in the PET-MR imaging system of FIG. 1 according to an embodiment of the invention.
Figure 3:
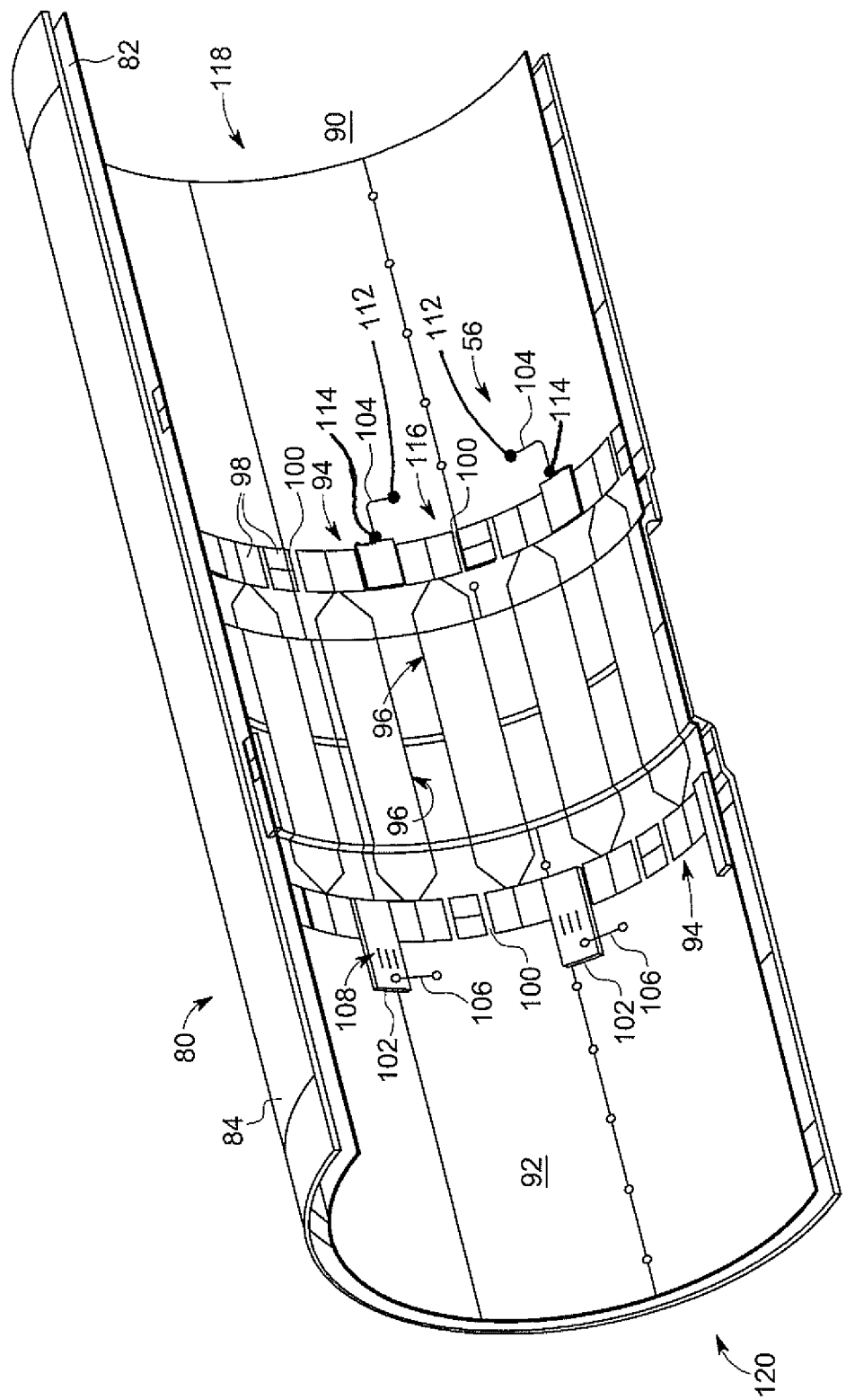

Referring now to FIGS. 2 and 3, an RF coil assembly 80 that is included in the hybrid PET-MR imaging system 10 is shown, although it is recognized that RF coil assembly 80 could also be implemented for use in other stand-alone MRI systems or other hybrid MRI systems. The RF coil assembly 80 includes an RF coil former or tube 82, an RF shield 84, and the RF body coil 56. According to an embodiment of the invention, the RF shield 84 is formed of stainless steel mesh and the RF coil former 82 is composed of fiberglass or fiber reinforced plastic (FRP) cylinders on the radially inner and radially outer surfaces, with a foam material sandwiched between the inner and outer surfaces, although it is recognized that other suitable materials could also be used. The RF shield 84 is positioned on the outer surface 88 of RF coil former 82 and is formed there about. The RF coil 56 is formed on an inner surface 92 of RF coil former 82 with an annular receiving or imaging area 90 (i.e., patient bore), and is separated radially from gradient coils 50 by RF shield 84, with the RF shield 84 functioning to de-couple the RF coils 56 from the gradient coils 50 (FIG. 1) in the PET-MR imaging system 10.

The positioning of RF coil 56 on the inner surface 92 of RF coil former 82 is shown in FIG. 3. The RF coil 56 is, in general, configured as a standard birdcage resonator that includes a pair of end rings 94 and a plurality of rungs 96 extending between the end rings 94. Each of end rings 94 is composed of a plurality of segments 98, with capacitors 100 being positioned between the segments 98. Decoupling networks or boards 102 are also positioned on end rings 94 of RF coil 56 to decouple the RF coil 56 from other coils in the bore. RF power cables 104 and DC power cables 106 provide power to RF coil 56 and decoupling boards 102 respectively, with chokes 108 on the decoupling boards 102 functioning to separate the RF circuit from the DC circuit.

Each of FIGS. 2 and 3 shows the placement/arrangement of the RF power cables 104 and DC power cables 106 in RF coil assembly 80 to provide power to the RF coil 56 and the decoupling networks 102, respectively. According to an exemplary embodiment of the invention, the RF and DC power cables 104, 106 are routed almost entirely along an outer surface 110 of RF shield 84 in order to prevent a high E-field from inducing a large common mode current on the shields of the respective cables, with cable shields 111 positioned about the respective cables being soldered to the RF shield to hold them in place. The RF power cables 104 are thus electrically connected to the RF shield 84. Holes 112 are formed in RF shield 84 and RF coil former 82 to provide for routing of the RF power cables 104 and the DC power cable 106 to the inner surface 92 of RF coil former 82, such that the RF power cables 104 and the DC power cables 106 can be connected to RF coil 56 and decoupling networks 102, respectively.

With respect to the plurality of RF power cables 104 (i.e., the "RF power cable arrangement"), and as shown in FIG. 3, it is seen that the RF power cables 104 are soldered to one of the end rings 94 of RF coil 56 at desired drive points 114, along an outer edge 116 of the chosen end ring 94 (i.e., on a side opposite/distal from the rungs 96). The RF power cables 104 may be connected to either the end ring 94 positioned generally at what is referred to as the "service end" 118 of the RF coil assembly 80 or to the end ring 94 positioned generally at what is referred to as the "patient end" 120 of the RF coil assembly 80—however, it is emphasized that the RF power cables 104 are connected to only one of the two end rings 94 (e.g., at the service end 118 end ring 94 in FIG. 3). This placement/arrangement of the RF power cables 104 for connection to RF coil 56 beneficially minimizes/eliminates transmit E-field induced currents on the shield of the RF power cables 104.

According to embodiments of the invention, the number of RF power cables 104 employed to drive the RF coil 56 can vary based on a design choice; however, the RF power cables 104 are provided as a multiple of two (e.g., 2, 4, 6, 8, etc.). As one example, for an RF coil 56 having sixteen rungs 96, four RF power cables 104 could be used to drive the RF coil 56, with the RF coil being driven in quadrature (i.e., RF power cables are 90 degrees apart in phase). As additional examples, for an RF coil 56 having sixteen rungs 96, eight RF power cables 104 could be used to drive the RF coil 56, with the RF power cables being 45 degrees apart in phase, or twelve RF power cables 104 could be used to drive the RF coil 56, with the RF power cables being 30 degrees apart in phase.

Beneficially, embodiments of the invention thus provide an arrangement for RF power cables 104 for use in a PET-MR imaging system that is configured to minimize the loss/attenuation of PET singles in the PET-MR system. The RF power cable arrangement also minimizes the shield currents present on the RF power cables 104 without the need for additional shielding and/or redesign of the magnet/gradient coil.

Therefore, according to one embodiment of the invention, a PET-MR apparatus includes a magnetic resonance (MR) imaging system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest. The PET-MR apparatus also includes a positron emission tomography (PET) system having a detector array positioned to encircle the bore to acquire PET emissions of the subject of interest and a plurality of RF power cables to provide power to the RF coil. The RF coil of the PET-MR apparatus comprises an RF body coil including a pair of end rings and a plurality of rungs extending between the end rings, wherein the plurality of RF power cables are coupled to one of the pair of end rings, along an outer edge of the one end ring distal from the plurality of rungs.

According to another embodiment of the invention, a PET-MR apparatus includes an MR imaging system having a plurality of gradient coils positioned about a patient bore, an RF coil former having inner and outer surfaces, an RF shield formed about the outer surface of the RF coil former, and an RF coil configured to emit an RF pulse sequence and receive resulting MR signals from a subject of interest, the RF coil comprising a bird-cage coil positioned on the inner surface of the RF coil former and including a pair of end rings and a plurality of rungs extending between the end rings. The PET-MR apparatus also includes a PET system having a detector array positioned to encircle the bore, with the detector array being controlled to acquire PET emissions of the subject of interest. The PET-MR apparatus further includes an RF power cable arrangement connected to one of the pair of end rings at a plurality of drive points located along an outer edge of the one end ring.

According to yet another embodiment of the invention, an RF coil assembly for use in a PET-MR imaging system includes a generally cylindrical RF coil former having an inner surface and an outer surface, an RF shield affixed to the outer surface of the RF coil former, and an RF body coil affixed to an inward facing surface of the RF coil former, with the RF body coil further including a pair of end rings and a plurality of rungs extending between the end rings. The RF coil assembly also includes a plurality of RF power cables to provide power to the RF body coil, with the plurality of RF power cables being coupled to one of the pair of end rings, along an outer edge of the one end ring distal from the plurality of rungs.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A PET-MR apparatus comprising:
   a magnetic resonance (MR) imaging system having a plurality of gradient coils positioned about a patient bore, an RF coil former having inner and outer surfaces, an RF shield formed about the outer surface of the RF coil former, and an RF coil positioned on the inner surface of the RF coil former, with the RF coil coupled to a pulse generator to emit an RF pulse sequence and receive resulting MR signals from a subject of interest;
   a positron emission tomography (PET) system having a detector array positioned to encircle the bore, with the detector array being controlled to acquire PET emissions of the subject of interest; and
   a plurality of RF power cables to provide power to the RF coil;
   wherein the RF coil comprises an RF body coil including:
      a pair of end rings; and
      a plurality of rungs extending between the end rings;
   wherein each of the pair of end rings includes:
      an inner edge where the plurality of rungs are joined to the end ring; and
      an outer edge opposite from the inner edge and distal from the plurality of rungs;
   wherein a plurality of holes are formed through the RF coil former and the RF shield outside of and spaced apart from the outer edge of the pair of end rings providing an opening for routing the plurality of RF power cables to the inner surface of the RF coil former; and
   wherein the plurality of RF power cables are coupled to one of the pair of end rings along the outer edge of the one of the pair of end rings.

2. The PET-MR apparatus of claim 1, further comprising a plurality of decoupling networks positioned on the end rings of the RF coil.

3. The PET-MR apparatus of claim 2, further comprising a plurality of DC power cables to provide power to the plurality of decoupling networks.

4. The PET-MR apparatus of claim 1, wherein the plurality of RF power cables are electrically connected to the RF shield.

5. The PET-MR apparatus of claim 1, wherein the plurality of RF power cables comprises an even number of RF power cables.

6. The PET-MR apparatus of claim 1, wherein each of the plurality of RF power cables is off in phase from another of the plurality of RF power cables for driving the RF body coil.

7. The PET-MR apparatus of claim 1, wherein the RF power cables are off in phase from one another by 30 degrees, 45 degrees, or 90 degrees.

8. The PET-MR apparatus of claim 1, wherein the RF body coil is driven in quadrature by the plurality of RF power cables.

9. The PET-MR apparatus of claim 1, wherein attachment of the plurality of RF power cables to the outer edge of one of the pair of end rings eliminates a shield current from the RF power cables and reduces PET attenuation or signal loss in the bore from the RF power cables.

10. The PET-MR apparatus of claim 1, further comprising cable shields positioned about the plurality of RF power cables, the cable shields being soldered to the RF shield.

11. A PET-MR apparatus comprising:
    a magnetic resonance (MR) imaging system including:
       a plurality of gradient coils positioned about a patient bore;
       an RF coil former having inner and outer surfaces;
       an RF shield formed about the outer surface of the RF coil former; and
       an RF coil configured to emit an RF pulse sequence and receive resulting MR signals from a subject of interest, the RF coil comprising a bird-cage coil positioned on the inner surface of the RF coil former and including a pair of end rings and a plurality of rungs extending between the end rings;
    a positron emission tomography (PET) system having a detector array positioned to encircle the bore, with the detector array being controlled to acquire PET emissions of the subject of interest; and
    an RF power cable arrangement connected to one of the pair of end rings at a plurality of drive points located along an outer edge of one of the pair of end rings, with the outer edge being opposite an inner edge at which the plurality of rungs is joined to the end ring;
    wherein a plurality of holes are formed through the RF coil former and the RF shield outside of and spaced apart from the outer edge of the pair of end rings providing an opening for routing the RF power cable arrangement to the inner surface of the RF coil former.

12. The PET-MR apparatus of claim 11, wherein the outer edge of the one end ring comprises an edge opposite from where the plurality of rungs are joined to the end ring.

13. The PET-MR apparatus of claim 11, further comprising a cable shield positioned about each of the RF power cables, the cable shields being soldered to the RF shield to electrically connect the RF power cables to the RF shield.

14. The PET-MR apparatus of claim 11, wherein the plurality of drive points comprises an even number of drive points corresponding to an even number of RF power cables included in the RF power cable arrangement.

15. The PET-MR apparatus of claim 14, wherein the number of RF power cables comprises an even number of RF power cables, with each of the RF power cables being off in phase from other RF power cables in driving the RF body coil.

16. The PET-MR apparatus of claim 11, wherein connecting of the RF power cable arrangement to the outer edge of one of the pair of end rings eliminates a shield current from the RF power cables and reduces PET attenuation or signal loss in the bore from the RF power cables.

17. An RF coil assembly for use in a PET-MR imaging system, the RF coil assembly comprising:
   a generally cylindrical RF coil former having an inner surface and an outer surface;
   an RF shield affixed to the outer surface of the RF coil former,
   an RF body coil affixed to an inward facing surface of the RF coil former, the RF body coil comprising:
      a pair of end rings; and
      a plurality of rungs extending between the end rings;
   wherein each of the pair of end rings includes:
      an inner edge where the plurality of rungs are joined to the end ring; and
      an outer edge opposite from the inner edge and distal from the plurality of rungs; and
   a plurality of RF power cables to provide power to the RF body coil, the plurality of RF power cables being coupled to one of the pair of end rings; along the outer edge of one of the pair end rings; and
   wherein a plurality of holes are formed through the RF coil former and the RF shield outside of and spaced apart from the outer edge of the pair of end rings providing an opening for routing the plurality of RF power cables to the inner surface of the RF coil former.

18. The RF coil assembly of claim 17, wherein connecting of the plurality of RF power cables to the outer edge of one of the pair of end rings eliminates a shield current from the plurality of RF power cables and reduces PET attenuation or signal loss in an imaging volume resulting from the RF power cables.

* * * * *